US00PP14536P39

(12) United States Plant Patent
Arisz

(10) Patent No.: US PP14,536 P3
(45) Date of Patent: Feb. 17, 2004

(54) SYMPHORICARPOS×DOORENBOSII PLANT NAMED 'ARISO'

(50) Latin Name: *Symphoricarpos×doorenbosii*
Varietal Denomination: Ariso

(75) Inventor: Catharina M. Arisz, Beverwijk (NL)

(73) Assignee: Pride of Place Plants, Inc. (CA)

( * ) Notice: Subject to any disclaimer, the term of this patent is extended or adjusted under 35 U.S.C. 154(b) by 0 days.

(21) Appl. No.: 10/052,646

(22) Filed: Jan. 18, 2002

(65) Prior Publication Data

US 2003/0150029 P1 Aug. 7, 2003

(51) Int. Cl.[7] ..... A01H 5/00

(52) U.S. Cl. ..... Plt./226

(58) Field of Search ..... Plt./226

*Primary Examiner*—Kent Bell

(74) *Attorney, Agent, or Firm*—Christie, Parker & Hale, LLP

(57) ABSTRACT

A new and distinct *Symphoricarpos×doorenbosii* plant with attractive red-purple fruit.

1 Drawing Sheet

Latin name of the genus of the species of the plant claimed: *Symphoricarpos×doorenbosii.*
Variety denomination: 'Ariso'.

BACKGROUND OF THE INVENTION

The present invention relates to a new and distinct variety of *Symphoricarpos×doorenbosii* plant named 'Ariso'. The new variety was created by self crossing *Symphoricarpos× doorenbosii* 'Mother of Pearl'. The varietal denomination of the new variety is 'Ariso'.

SUMMARY OF THE INVENTION

Among the novel characteristics possessed by the new variety which distinguishes it from its parents and all other varieties of which I am aware, are its attractive red-purple fruit.

Asexual reproduction by propagation of vegetative cuttings of the new variety as performed in The Netherlands shows that the foregoing and other distinguishing characteristics come true to form and are established and transmitted through succeeding propagations.

COMPARISON WITH PARENTS

Fruit of 'Ariso' differ from *Symphoricarpos×doorenbosii* 'Mother of Pearl' in having bright red-purple color with lighter blotches whereas 'Mother of Pearl' have lighter to almost white fruit.

BRIEF DESCRIPTION OF ILLUSTRATION

The accompanying photograph illustrates a typical specimen of the fruit and foliage of the new variety depicted in color as nearly true as it is reasonably possible to make in a color illustration of this character.

DESCRIPTION OF THE NEW VARIETY

The following is a detailed description of the new variety with color terminology, references and/or values in accordance with The Royal Horticultural Society Colour Chart (R.H.S.C.C.). The terminology used in the color descriptions herein refers to plate numbers in the aforementioned color chart except where common terms of color definition are employed. Phenotypic expression may vary with environmental, cultural and climatic conditions, as well as differences in conditions of light and soil.

The following observations are made of specimens of 2-year-old plants grown outdoors in The Netherlands. The range of average Summer day temperature is ±18° C. and average Summer night temperature is ±10° C. No photoperiodic treatments or growth retardants were used.

Plant:

*Crop time.*—Approximately 1 year from rooted cuttings; field grown.

*Growth habit.*—Broad upright/spreading with arching branches. Vigor: Growth rate/vigor is moderate to vigorous, growing an average of about 85 cm per season.

*Plant shape.*—Broad, flattened globe-shaped. Size: Height about 1 m; diameter or area of spread about 1.25 m.

*Branching habit.*—Free branching: main shoots appear from base. Pinching Required: No pinching required. Lateral Branches: Average quantity 16; length average 16 cm (shorter towards the top); diameter average 1.5 mm, color near 143B to 143C, aging to near 175A to 175B. Internode: Average length 4.5 cm. Stem: Stems slightly exfoliating when older (only at the base); color brown, near 175A to 175B. Pubescence: No.

*Leaves.*—Arrangement: Opposite; singly borne. Quantity per lateral branch: Average 12 (between 8 to 14). Shape: Broad — elliptic to almost round; tip retuse to rounded, sometimes mucronate; base obtuse to slightly alternate. Size: Length on main stems, average 3.5 cm, on lateral branches, average 2 cm; width on main stems average 3.5 cm, on lateral branches average 2.4 cm. Texture: Slightly rugose, dull.

Pubescence: No leaf pubescence. Margin: Entire occasionally with 1 or 2 deep crenate lobes). Venation Pattern: Pinnate. Color: Immature leaves upper side dark-green, near 139A; under side greyish-green, near 131A; mature leaves upper side dark-green, near 139A, under side greyish-green, near 131A. Vein color: Upper side main view green, near 143A; under side main view green near 143A.

*Petiole.*—Length up to about 4 mm (average about 3 mm); diameter about 1 mm; color green, near 143A.

*Durability of foliage to stresses.*—High.

*Stipules, tendrils, thorns, spines or prickles.*—None.

Flower:

*Arrangement.*—Terminal panicle and axillary panicles from leaf axils.

*Form.*—Campanulate.

*Quantity.*—Average 20 buds and flowers per lateral stem; more than 1,000 buds and flowers per plant.

*Flowering season.*—In The Netherlands in August through September.

*Time to flower or response time.*—One year.

*Rate of opening.*—Approximately 20% per panicle at once.

*Fragrance.*—None.

*Aspect.*—Campanulate.

*Shape.*—Campanulate.

*Size.*—Diameter about 4 mm; depth or height about 5 mm.

*Longevity.*—A few days on the plant; a few days as a cut flower.

*Persistence.*—Self cleaning.

*Petalage.*—Appearance: Dull, smooth. Texture: Smooth. Arrangement: Rotate, partially fused. Number: About 5. Fused: Partly fused, top ⅓rd free. Shape: Oval to elliptic. Margin: Entire. Tip: Shallowly incised/praemorse to almost entire. Size: Length about 5 mm; width about 3 mm. Color: When opening upper side greenish-white near 137C, under side greyish-purple near 185D or lighter to almost white; when fully opened upper side greenish-white near 157C, under side greyish-purple near 188D or lighter to almost white, color does not fade. Petaloids: None. Sepals: Appearance dull, smooth texture; funnel form arrangement. Quantity: About 5. Margin: Entire. Tip: Acuminate. Color: Upper side near 143A, sometimes with small greyish-purple blotches near 184A; under side green near 143A. Calyx: Funnel form shaped, length about 4 mm (including ovary); diameter about 2 mm. Peduncle: Length about 1.1 cm, diameter about 1 mm, peduncle angle about 45°, peduncle strength moderate, peduncle color near 143B. Bud: Oval shape; length about 5 mm; diameter about 3 mm; color greyish-purple, near 185D or lighter to pale yellowish-green 195C. Rate of opening: Approximately 20% at once per panicle. Stamens: About 5. Anthers: Narrow, oblong; about 1 mm, color creamy-white. Pistils: Usually 1, length about 3 mm. Stigma: Club shaped, color light-green near 155C. Styles: Length about 2.5 mm; color very light-green near 145D. Ovary: Green near 143A, sometimes with a small greyish-purple bottom near 184A.

*Fruit.*—Average fruit per flower is about 1, number of days to fruit ripening about 30, fruit shape globular, fruit length average about 12 mm, fruit width average about 13 mm, fruit texture smooth and only slightly glossy, fruit color near 67A to 67B, often with lighter blotches near 70B.

*Seeds.*—Seeds are produced; seed diameter average 13 mm (between 10 to 14 mm); color red-purple near 67A to 67B often with lighter near 70B blotch; average 2 seeds per fruit, seed shape broad elliptic, average length about 2 mm, average width about 1.5 mm, fruit shape globular.

*Pollen.*—Pollen is scarce but sometimes produced, color near 158D.

*Disease resistance.*—Not known.

*Temperature tolerance.*—High temperature tolerance is to 35° C.; low temperature tolerance is to USDA zone 4.

I claim:

1. A new and distinct *Symphoricarpos×doorenbosii* plant of the variety substantially as shown and described.

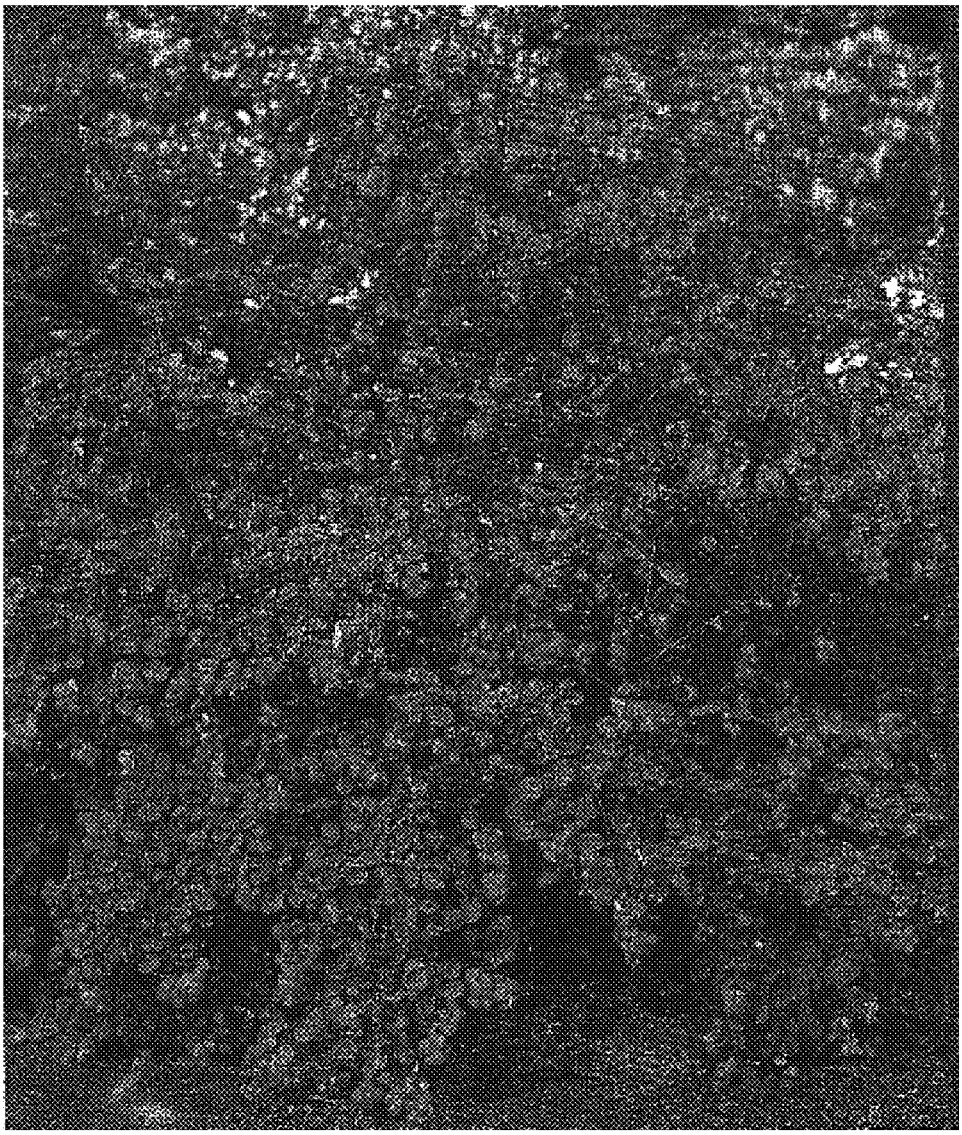

* * * * *